US010629304B2

(12) United States Patent
Leon et al.

(10) Patent No.: US 10,629,304 B2
(45) Date of Patent: Apr. 21, 2020

(54) SYSTEMS AND METHODS FOR DECISION SUPPORT FOR ANIMAL HEALTH QUERIES

(71) Applicant: Whiskers Worldwide, LLC, Skokie, IL (US)

(72) Inventors: Debra Leon, Long Grove, IL (US); Trevor Page, Chicago, IL (US); Gunnison Carbone, Orlando, FL (US)

(73) Assignee: Whiskers Worldwide, LLC, Skokie, IL (US)

( * ) Notice: Subject to any disclaimer, the term of this patent is extended or adjusted under 35 U.S.C. 154(b) by 686 days.

(21) Appl. No.: 15/359,033

(22) Filed: Nov. 22, 2016

(65) Prior Publication Data
US 2018/0144099 A1 May 24, 2018

Related U.S. Application Data

(63) Continuation-in-part of application No. 14/011,538, filed on Aug. 27, 2013, now abandoned.

(51) Int. Cl.
*G16H 50/20* (2018.01)
*G06N 5/04* (2006.01)
(Continued)

(52) U.S. Cl.
CPC ............. *G16H 50/20* (2018.01); *A61B 5/00* (2013.01); *G06N 5/041* (2013.01); *G06N 5/045* (2013.01);
(Continued)

(58) Field of Classification Search
CPC ........ G16H 50/20; G16H 50/30; G16H 10/20; G16H 19/345; G06N 5/045; H04L 67/02; H04L 67/42
(Continued)

(56) References Cited

U.S. PATENT DOCUMENTS 6,006,191 A 12/1999 DiRienzo
6,208,974 B1 * 3/2001 Campbell ............. G06F 19/328
705/3
(Continued)

FOREIGN PATENT DOCUMENTS

CA 2977383 A1 2/2019
CN 108920719 A 11/2018
(Continued)

OTHER PUBLICATIONS

Cheng et al., "caREMOTE: The Design of a Cancer Reporting and Monitoring Telemedicine System for Domestic Care" Aug. 30-Sep. 3, 2011 33rd Annual International Conference of the IEEE EMBS, pp. 3168-3171. (Year: 2011).*
(Continued)

*Primary Examiner* — Vincent Gonzales
*Assistant Examiner* — Chase P. Hinckley
(74) *Attorney, Agent, or Firm* — Beem Patent Law Firm (57) ABSTRACT

A decision support system is described that solves various technical problems associated with prior systems. The system may include a thin client application that downloads question sets from a server. The question sets may include a series of interlinked questions and answers as well as scores associated with the answers. Scores of selected answers may be tallied and a decision corresponding to the cumulative score of the selected answers may be provided to a user. As a result, the system may enable the ability to update (add, revise or delete) questions, answers and question lines without needing to recompile and redistribute the client application. In addition, the transmission of a complete question set reduces overall network traffic and technical problems arising from network disruptions among other technical benefits.

6 Claims, 9 Drawing Sheets

(51) Int. Cl.

| | | |
|---|---|---|
| *H04L 29/08* | (2006.01) | |
| *G16H 10/20* | (2018.01) | |
| *G16H 50/30* | (2018.01) | |
| *A61B 5/00* | (2006.01) | |
| *G06N 5/00* | (2006.01) | |

(52) U.S. Cl.
CPC ............. *G16H 10/20* (2018.01); *G16H 50/30* (2018.01); *H04L 67/02* (2013.01); *G06N 5/003* (2013.01)

(58) Field of Classification Search
USPC .......................................................... 706/46
See application file for complete search history.

(56) References Cited

U.S. PATENT DOCUMENTS

| | | | | |
|---|---|---|---|---|
| 7,076,437 | B1* | 7/2006 | Levy .................... | G06F 19/324 705/3 |
| 7,671,751 | B2* | 3/2010 | Russell ................. | G06Q 10/10 119/174 |
| 8,271,415 | B2 | 9/2012 | Iliff | |
| 10,149,617 | B2* | 12/2018 | Couse .................. | A01K 29/005 |
| 2001/0051765 | A1 | 12/2001 | Walker et al. | |
| 2003/0004655 | A1* | 1/2003 | Singh ................ | G06Q 30/0603 702/32 |
| 2003/0166996 | A1* | 9/2003 | Kim ..................... | A01K 29/00 600/300 |
| 2003/0212574 | A1* | 11/2003 | Olivier .................. | G06Q 30/02 705/2 |
| 2003/0229452 | A1* | 12/2003 | Lewis ................... | G06Q 50/24 702/19 |
| 2004/0230607 | A1* | 11/2004 | Pawlick ................ | A01K 11/008 |
| 2005/0032034 | A1* | 2/2005 | Dodds ................... | G06Q 50/24 435/4 |
| 2005/0108052 | A1* | 5/2005 | Omaboe ................ | G06Q 50/22 705/2 |
| 2006/0038010 | A1* | 2/2006 | Lucas ................... | G06Q 10/087 235/385 |
| 2006/0064250 | A1* | 3/2006 | Goldstein ........... | G06F 19/3456 702/19 |
| 2007/0143151 | A1 | 6/2007 | Fey et al. | |
| 2007/0174253 | A1* | 7/2007 | Hodnett ................ | G06Q 10/00 |
| 2007/0226257 | A1* | 9/2007 | Yarnall, Jr. ........... | G06Q 10/10 |
| 2008/0058670 | A1* | 3/2008 | Mainini ................ | A61B 5/0002 600/549 |
| 2008/0097809 | A1* | 4/2008 | Stroman ............... | G06Q 10/063 705/35 |
| 2008/0162175 | A1* | 7/2008 | Paige .................... | G06Q 10/00 705/1.1 |
| 2008/0312511 | A1* | 12/2008 | Osler ................... | A61B 5/0008 600/300 |
| 2009/0006419 | A1* | 1/2009 | Savitsky ............... | G06Q 10/00 |
| 2009/0062623 | A1 | 3/2009 | Cohen et al. | |
| 2009/0106044 | A1* | 4/2009 | Schweisguth .......... | A01K 15/02 705/2 |
| 2009/0138310 | A1* | 5/2009 | Beall ..................... | G06F 19/324 705/7.12 |
| 2009/0175980 | A1* | 7/2009 | Willcocks .............. | A23K 50/40 426/2 |
| 2009/0234916 | A1* | 9/2009 | Cosentino ............. | G16H 10/60 709/203 |
| 2010/0121156 | A1* | 5/2010 | Yoo ..................... | G06F 19/3418 600/300 |
| 2010/0261981 | A1* | 10/2010 | Griffioen ............ | A61B 5/02055 600/301 |
| 2011/0010380 | A1* | 1/2011 | Chen .................... | A01K 29/00 707/769 |
| 2011/0054978 | A1 | 3/2011 | Mohil | |
| 2011/0093295 | A1* | 4/2011 | Mankad ................ | G06Q 10/10 705/3 |
| 2011/0213625 | A1* | 9/2011 | Joao ..................... | G06F 19/328 705/3 |
| 2011/0302117 | A1* | 12/2011 | Pinckney ............... | G06Q 30/02 706/12 |
| 2013/0046552 | A1* | 2/2013 | Verstandig ............. | G06Q 30/02 705/2 |
| 2013/0095459 | A1* | 4/2013 | Tran ..................... | A61B 5/6816 434/247 |
| 2013/0096942 | A1* | 4/2013 | Bowles .................. | G06Q 50/22 705/2 |
| 2013/0173439 | A1* | 7/2013 | Christiansen ........ | G06Q 10/103 705/34 |
| 2013/0185097 | A1* | 7/2013 | Saria ..................... | G06Q 10/00 705/3 |
| 2013/0297553 | A1* | 11/2013 | Bierner ................. | G06N 20/00 706/52 |
| 2014/0019162 | A1* | 1/2014 | Skowronski ........... | G06Q 50/24 705/3 |
| 2014/0046698 | A1* | 2/2014 | Skocic ................ | G06F 21/6218 705/3 |
| 2014/0052463 | A1* | 2/2014 | Cashman ............... | G06Q 20/18 705/2 |
| 2014/0182519 | A1* | 7/2014 | Tupin, Jr. .............. | A01K 27/009 119/859 |
| 2014/0228648 | A1* | 8/2014 | Goldberg ............... | A01K 29/00 600/301 |
| 2014/0275824 | A1* | 9/2014 | Couse ..................... | G16H 40/60 600/301 |
| 2014/0304200 | A1* | 10/2014 | Wall ..................... | G06F 19/3418 706/12 |
| 2014/0316805 | A1 | 10/2014 | Nagata | |
| 2015/0057963 | A1* | 2/2015 | Zakharov ................ | A61B 5/01 702/131 |
| 2015/0363564 | A1 | 12/2015 | Lai et al. | |
| 2016/0063188 | A1 | 3/2016 | Thornberry et al. | |
| 2016/0192620 | A1 | 7/2016 | Hu et al. | |
| 2016/0246934 | A1 | 8/2016 | Dunlop | |

FOREIGN PATENT DOCUMENTS

| | | | |
|---|---|---|---|
| CN | 108935317 A | 12/2018 | |
| CN | 109036542 A | 12/2018 | |
| CN | 109064011 A | 12/2018 | |
| CN | 109064012 A | 12/2018 | |
| CN | 208211175 U | 12/2018 | |
| EP | 1892657 A1 * | 2/2008 | ........... G06Q 10/107 |
| EP | 2472487 A2 * | 7/2012 | ......... G08B 21/0423 |
| EP | 3264299 A1 | 3/2018 | |
| GB | 2347503 A * | 9/2000 | |
| JP | 2002197290 A * | 7/2002 | |
| JP | 2003-141240 | 5/2003 | |
| JP | 4688512 B2 * | 5/2011 | |
| JP | 4832948 B2 * | 12/2011 | |
| KR | 20030070866 A * | 9/2003 | |
| KR | 20060058446 A * | 5/2006 | |
| KR | 20180106592 A | 10/2018 | |
| WO | 2005029387 | 3/2005 | |
| WO | WO-2005029387 A1 * | 3/2005 | ............ G06Q 30/02 |
| WO | 2018118714 A1 | 6/2018 | |
| WO | 2019143714 A1 | 7/2019 | |

OTHER PUBLICATIONS

Madder et al., "e-Surveillance in Animal Health: use and evaluation of mobile tools" Apr. 2012 Parasitology 139, pp. 1831-1842. (Year: 2012).*
Li et al., "Decision Support System for the Response to Infectious Disease Emergencies Based on WebGIS and Mobile Services in China" Jan. 23, 2013, PLOS One, vol. 8, Issue 1, pp. 1-12. (Year: 2013).*
Sawford et al., "A Focused Ethnographic Study of Sri Lankan Government Field Veterinarians' Decision Making about Diagnostic Laboratory Submissions and Perceptions of Surveillance" Oct. 25, 2012, PLOS One, vol. 7, Issue 10, pp. 1-11. (Year: 2012).*
Robertson et al., "Mobile Phone-based Infectious Disease Surveillance System, Sri Lanka" Oct. 2010, Emerging Infectious Diseases, vol. 16, No. 10, pp. 1524-1531. (Year: 2010).*

(56) References Cited

OTHER PUBLICATIONS

Kristensen et al., "A mixed methods inquiry: How dairy farmers perceive the value(s) of their involvement in an intensive dairy herd health management program" Dec. 18, 2008, Acta Veterinaria Scandinavia, pp. 1-12. (Year: 2008).*
Smedberg, Asa, "Enabling of Cross-Usage of Public Health Systems" 2008 IEEE Second International Conference on the Digital Society, pp. 102-106. (Year: 2008).*
Karimuribo et al., "Towards One Health disease surveillance: The Southern African Centre for Infectious Disease Surveillance approach" 2012 Onderstepoort Journal of Veterinary Research 79(2), pp. 1-7. (Year: 2012).*
Lin et al., "Addressing Animal Health Knowledge Gaps in Southern Countries: The Creation of a 2D Animal Health Resource Room" 2009, EJISDC, vol. 39, No. 6, pp. 1-27. (Year: 2009).*
Langstaff, Ian G, "Smart Surveillance with smartphones" Dec. 2012, Australian Veterinary Journal, vol. 91, No. 12. (Year: 2012).*
Sawford, Kate Elizabeth, "Animal health surveillance for early detection of emerging infectious disease risks" Dec. 2011, Doctoral Thesis, University of Calgary, pp. i-234. (Year: 2011).*
Weaver, Alice Malia, "Fort Collins Veterinary Practices and Websites: How Telemedicine is used as a Marketing Tool" 2012, Masters Thesis, Colorado State University, pp. i-167. (Year: 2012).*
PetMD, available as of Jul. 18, 2013 at http://www.petmd.com/.
Web DVM, available as of Jul. 18, 2013 at http://web-dvm.net/.
ZOOTOO, available as of Jul. 18, 2013 at http://www.zootoo.com/.
HelpMyHound, available as of Jul. 18, 2013 at http://helpmyhound.com/.
HomeAgain, available as of Jul. 18, 2013 at http://public.homeagain.com/pet-emergency.html.
Veterinary Partner, available as of Jul. 18, 2013 at http://www.veterinarypartner.com/.
Justanswer. Pet, available as of Jul. 18, 2013 at http://www.justanswer.com/pet/.
Pet WebMD, available as of Jul. 18, 2013 at http://pets.webmd.com/.
Veterinarian Advice Online, available as of Jul. 18, 2013 at http://www.free-online-veterinarian-advice.com/.
AskVetAdvice.com, available as of Jul. 18, 2013 at http://www.askvetadvice.com/.
AskAVetQuestion.com, available as of Jul. 18, 2013 at http://www.askavetquestion.com/.
www.webMD.com/phr—Apr. 21, 2012—https://web.archive.org/web/20120421063410/http://www.webmd.com/phr.
PetMD.com—Jun. 1, 2012—(https://web.archive.org/web/20120601174536/http://www.petmd.com/).
PetMD.com App Article—Oct. 18, 2012—(http://www.petmd.com/news/care-safety/nws_multi_cat_dog_symptom_checker_app_launch-29241).
Thakre et al. Zigbee Based Health Monitoring and Feedback System in Animal Health Care. International Journal of Innovative Research in Science, Engineering and Technology, vol. 6, Special Issue 11, May 2017. (5 pages).
Kumar et al. Dog Health Management Trainer: An Effective eLearning System for Dog Owners and Practitioners. Journal of the Indian Society of Agricultural Statistics, 70(1) 2016, pp. 83-89. (8 pages).
Johnson et al. An Innovative New Approach to Animal Care. IEEE. 2018. (2 pages).
Bhavsar et al. ZigBee Based Network Architecture for Animal Health Monitoring. IEEE. Sep. 4-5, 2015. (2 pages).

* cited by examiner

SYSTEMS AND METHODS FOR DECISION SUPPORT FOR ANIMAL HEALTH QUERIES

PRIORITY

This application is a continuation-in-part of U.S. application Ser. No. 14/011,538 filed Aug. 27, 2013, which is hereby incorporated by reference in its entirety.

The claims in the instant application are different than those of the parent application or other related applications. The Applicant therefore rescinds any disclaimer of claim scope made in the parent application or any predecessor application in relation to the instant application. Any such previous disclaimer and any cited references may need to be revisited. Further, any disclaimer made in the instant application should not be read into or against the parent application.

BACKGROUND OF THE INVENTION

Technical Field

The invention relates generally to a decision support system and method, and more specifically to a pet health query answering system and method.

Related Art

Traditionally, when a pet is acting differently than normal or even exhibiting concerning symptoms, the pet owner's only option is to take the pet to a doctor of veterinary medicine ("veterinarian," "DVM", "VMD" or "vet"). If the situation occurs after hours, the options are more limited and costly. In addition, access to a Veterinary Emergency Clinic is often limited by geography (clinics can be hundreds of miles away). While taking the pet to a veterinarian is often the right course of action, in many situations it is not necessary to take a pet to a veterinarian immediately, if at all.

At the same time, the pet owner likely does not have sufficient knowledge to fully appreciate the mildness or severity of the pet's condition, so the owner may not know whether the pet's malady is serious enough as to require immediate attention or whether it is something that may be monitored and managed without professional intervention. In these situations, the owner may elect to err on the side of caution and bring the pet to the vet, even when it turns out that a more passive approach may be sufficient. While the owner has the pet's best interests in mind, these frequent visits to a DVM in non-emergency situations may become expensive and inconvenient for the pet owner. This is also an inefficient use of DVM resources and may delay care for animals in immediate need of DVM care. In addition, a common issue for dogs and cats is anxiety, which is exacerbated by a visit to a vet; as a result, unnecessary veterinary visits can have adverse health impact on the pet. Cats in particular are prone to severe anxiety when transported in a car and taken away from their familiar environment.

In some existing systems, stand-alone applications are used to provide pet medical advice to users. Typically, the questions and answers in these stand-alone applications are integrated into the executable file for the application or other locally stored application files. This approach has several drawbacks. For example, whenever the content of the tutorial needs to be changed or updated, the entire application needs to be recompiled and redistributed to each user. This is difficult on the application developer as they must have knowledge of the code to know what to change and must take care to avoid causing errors in other aspects of the code. Additionally, this may require approval from a third party for the new application, such as on mobile phone app stores, to release the latest tutorial, which can lead to delays. This also requires users to maintain the most current, up-to-date version of the application installed to access the latest version of a tutorial. If a user does not update the application, she may be accessing an out-of-date or incorrect tutorial.

Others have used web-based tutorials to provide medical advice to users. This approach also suffers drawbacks however, such as requiring a constant internet connection. If at any point in the tutorial, a user loses an internet connection, their place in the tutorial is lost and they will be required to restart the tutorial, requiring more time and computer resources. Moreover, none of the above-mentioned systems incorporate the specifics of each individual pet into the algorithm so that the answers are general and may not accurately reflect the necessary information for a specific pet.

Accordingly, a need has long existed for improved decision support systems and methods for answering a pet health query.

SUMMARY

A decision support system is described that solves various technical problems associated with prior systems. The system may include a thin client application that downloads question sets from a server. The question sets may include a series of interlinked questions and answers as well as scores associated with the answers. Scores of selected answers may be tallied and a decision corresponding to the cumulative score of the selected answers may be provided to a user. As a result, the system may enable the ability to update (add, revise or delete) questions, answers and question lines without needing to recompile and redistribute the client application. In addition, the transmission of a complete question set reduces overall network traffic and technical problems arising from network disruptions among other technical benefits.

In one embodiment, a system for providing animal related health care decision support is provided. The system may include a software module for use on a mobile device, the software module including instructions stored on a non-transitory computer readable medium that: present an animal related health topic to a user; receive a selection of the animal related health topic from the user; request, from a server computer, a question set related to the selected animal related health topic, the question set including one or more questions, each question having one or more associated answers; receive, from the server computer, the question set; display one or more questions from the question set; receive selections of answers associated with the displayed questions; determine a course of action based on the selected answers; and display the determined course of action.

In another embodiment, a method for providing decision support may be provided. The method may include: presenting an animal related health topic to a user; receiving a selection of the animal related health topic from the user; requesting, from a server computer, a question set related to the selected animal related health topic, the question set including one or more questions, each question having one or more associated answers; receiving, from the server computer, the question set; displaying one or more questions from the question set; receiving selections of answers associated with the displayed questions; determining a course of action based on the selected answers; and displaying the determined course of action.

In still another embodiment, a system for providing animal related health care decision support may be provided. The system may include a first software module for use on a mobile device, the software module including instructions stored on a non-transitory computer readable medium that: present an animal related health topic to a user; receive a selection of the animal related health topic from the user; request, from a server computer, a question set related to the selected animal related health topic, the question set including one or more questions, each question having one or more associated answers; receive, from the server computer, the question set; display one or more questions from the question set; receive selections of answers associated with the displayed questions; determine a course of action based on the selected answers; and display the determined course of action. The system also may include a second software module for use on a server computer, the second software module including instructions stored on a non-transitory computer readable medium that: receive the request for the question set related to the selected animal related health topic; and transmit a question set related to the selected animal related health topic, the question set including one or more questions, each question having one or more associated answers.

Other systems, methods, features, and technical advantages of the invention will be, or will become apparent to one with skill in the art upon examination of the following figures and detailed description. It is intended that all such additional systems, methods, features, and technical advantages be included within this description, be within the scope of the invention, and be protected by the following claims.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION OF THE PREFERRED EMBODIMENTS

The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of systems and methods consistent with the contact management system architecture may be stored on, distributed across, or read from other machine-readable media, for example, secondary storage devices such as hard disks, floppy disks, and CD-ROMs; a signal received from a network; other forms of ROM or RAM either currently known or later developed; and the like.

Furthermore, although specific components of the communications architecture will be described, methods, systems, and articles of manufacture consistent with the decision support system architecture may include additional or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, and other data structures may be separately stored and managed, may be incorporated into a single memory or database, may be distributed, or may be logically and physically organized in many different ways, including unstructured data. Programs may be parts of a single program, separate programs, or distributed across several memories and processors. Systems may be implemented in hardware, software, or a combination of hardware and software in one processing system or distributed across multiple processing systems.

While the system may be used to implement decision support in various areas, it may be particularly well suited to the realm of pet health care decision support. In that regard, the system may receive a plurality of user inputs relating to user observations or subjective assessments with the goal of recommending a next course of action from among a plurality of possible options.

1.0 Exemplary Decision Support System Overview

Figure 1:
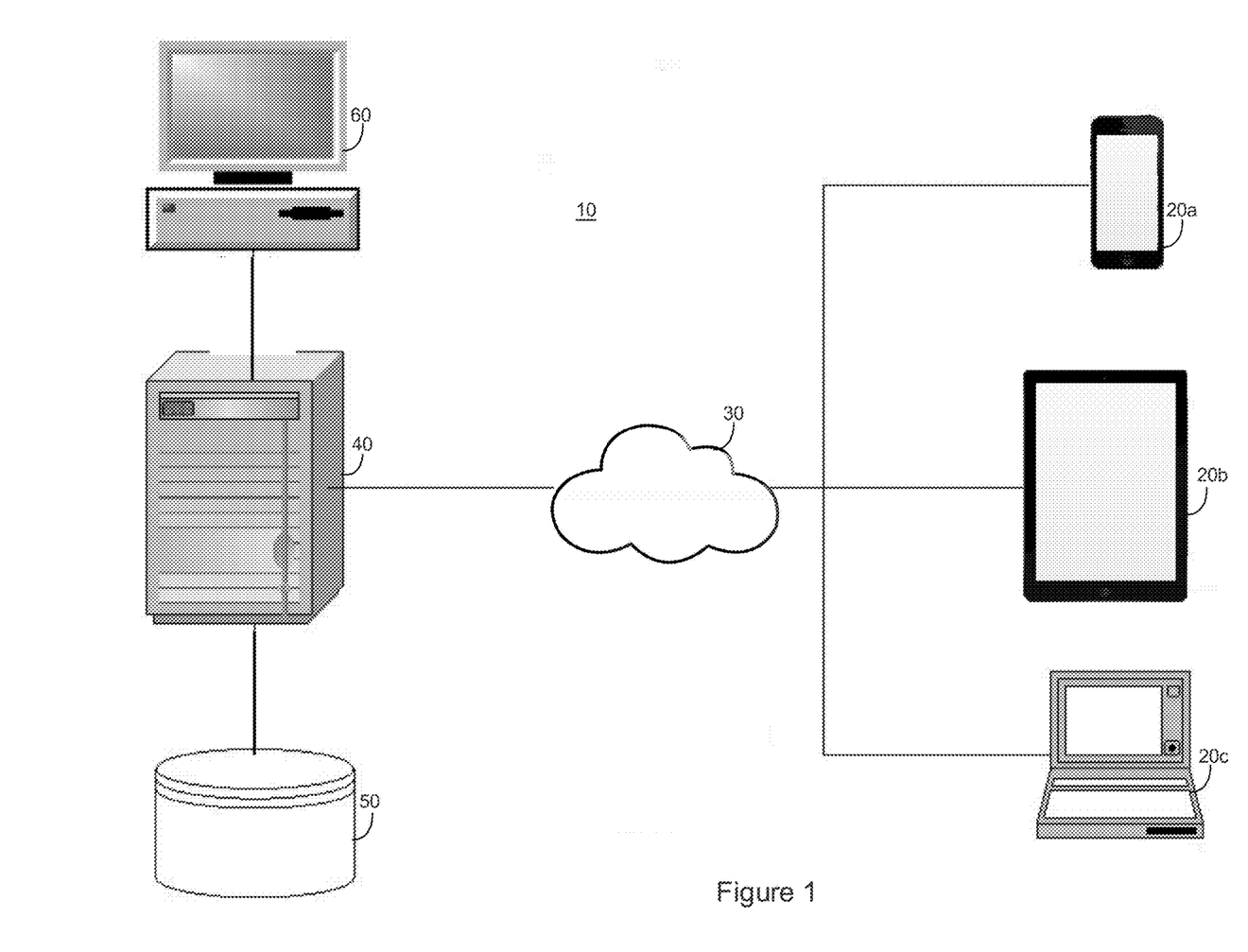
FIG. 1 shows an exemplary physical architecture for an exemplary system for answering a pet health query.

Referring to FIG. 1, an exemplary physical architecture 10 for a decision support system 10 for answering pet health queries is shown. One or more client devices may run client applications 20a-c that may communicate with a decision support server 40 via a communications network 30 (shown as an exemplary Internet cloud). The client applications 20a-c may request pet health topics, questions, and/or answers from the server 40 and present the same to a user. The client applications 20a-c also may receive input from the user, such as user selections of answers to questions, user profile information and the like, and determine an appropriate course of action based on the user's selections and present that course of action to a user, among other functions described herein. The decision support server 40 may provide the topics, questions, and/or answers to client applications 20a-c based on received requests, such as queries and the like. The decision support server 40 also may store information in a database 50 and also may provide an administration interface 60 that enables an administrator to interact with the server 40.

Although references will now be made to specific components of the system performing specific features, it should be apparent to one of ordinary skill in the art that such references are exemplary and are not intended to limit the scope of the claims in any way; furthermore, the functionalities described herein may be implemented in a virtually unlimited number of configurations. For example, although figuratively attached to the server 40, the database 50 may, in practice, distribute user-specific data elements directly to one or more client systems 20a, 20b, and 20c. Similarly, the server 40 may be implemented as a single server configured to provide all of the system's functionalities, or the functionalities may be implemented across multiple servers.

1.1 Exemplary Client Applications 20a-c

The client applications 20a-c may provide a user interface for the system 10 and may communicate user profile and other information with the server 40 via communications network 30. In one embodiment, client applications 20a-c may comprise stand-alone applications which may be either platform dependent or platform independent. For example, client applications 20a-c may be stand-alone applications for a mobile phone configured to run on a mobile operating system such as the iOS™ operating system from Apple Inc. located in Cupertino, Calif., the Android™ operating system from Google, Inc. located in Mountain View, Calif., or the like. Alternatively, or additionally, client applications 20a-c may connect to the server 40 via the Internet using a standard browser application. Alternatively, or additionally, one or more of the client applications 20a-c may be an application configured to run on mobile computer such as a laptop computer, handheld computer, tablet, mobile messaging device, or the like which may all utilize different hardware and/or software packages. Other methods may be used to implement the client applications 20a-c.

In operation, client systems 20a-c may operate in conjunction with decision support server 40, for example, to allow a user to register with the server 40, enter health information about their pet, conduct pet health topic searches, answer pet health related questions, receive recommendations for veterinary care and the like. Client application 20a-c also may provide other functions, such as present options for users to look up pet help by category, present information about relevant products and knowledge bases, contact a veterinarian by email, chat or voice communication channels, find a local veterinarian, and the like. As should be apparent to one of ordinary skill in the art from the disclosure herein, other related services may also be provided.

A user may be an individual, a commercial entity, or any other type of entity. For example, an individual user may be a person who owns a pet. Alternatively, or additionally, an individual user may be a person in temporary care of a pet. An exemplary commercial entity user may be a professional health care provider or a representative thereof, such as a veterinarian or the like.

1.2 Exemplary Communications Networks 30

The communications network 30 may be any type any private or public communication network, such as the Internet, and may include one or more communications networks. In some embodiments, the communications network 30 may be the Internet or the like.

1.3 Exemplary Decision Support Server 40

The decision support server 40 may store user profiles, pet health questions, pet health answers, and other information in a database 50, receive search requests from a client application 20a-c, communicate with various third parties (such as veterinarians and the like), provide a user interface for an administration application 60, and the like. In operation, the server 40 and client systems 20a-c may, for example, allow a user to register with the server 40, conduct pet health topic searches, provide recommendations for veterinary care, provide hyperlinks to relevant products and knowledge bases, and the like. As should be apparent to one of ordinary skill in the art from the disclosure herein, other related services may also be provided.

The database 50 may store a variety of information, including user profile information, user preference information, pet health question sets, pet health answers, decision trees, veterinary contact information, product hyperlinks, and the like. In some embodiments, all information stored in the database 50 is encrypted.

In some embodiments, the server 40 and database 50 may comprise one or more instances of a GoDaddy™ Virtual Private Server (provided by GoDaddy Operating Company, LLC of Scottsdale, Ariz.) running the Windows Server 2012™ operating system (provided by Microsoft Corporation of Redmond, Wash.) utilizing one or more of relational databases and/or other storage mechanisms.

1.4 Exemplary Administrative Application 60

Figure 6:
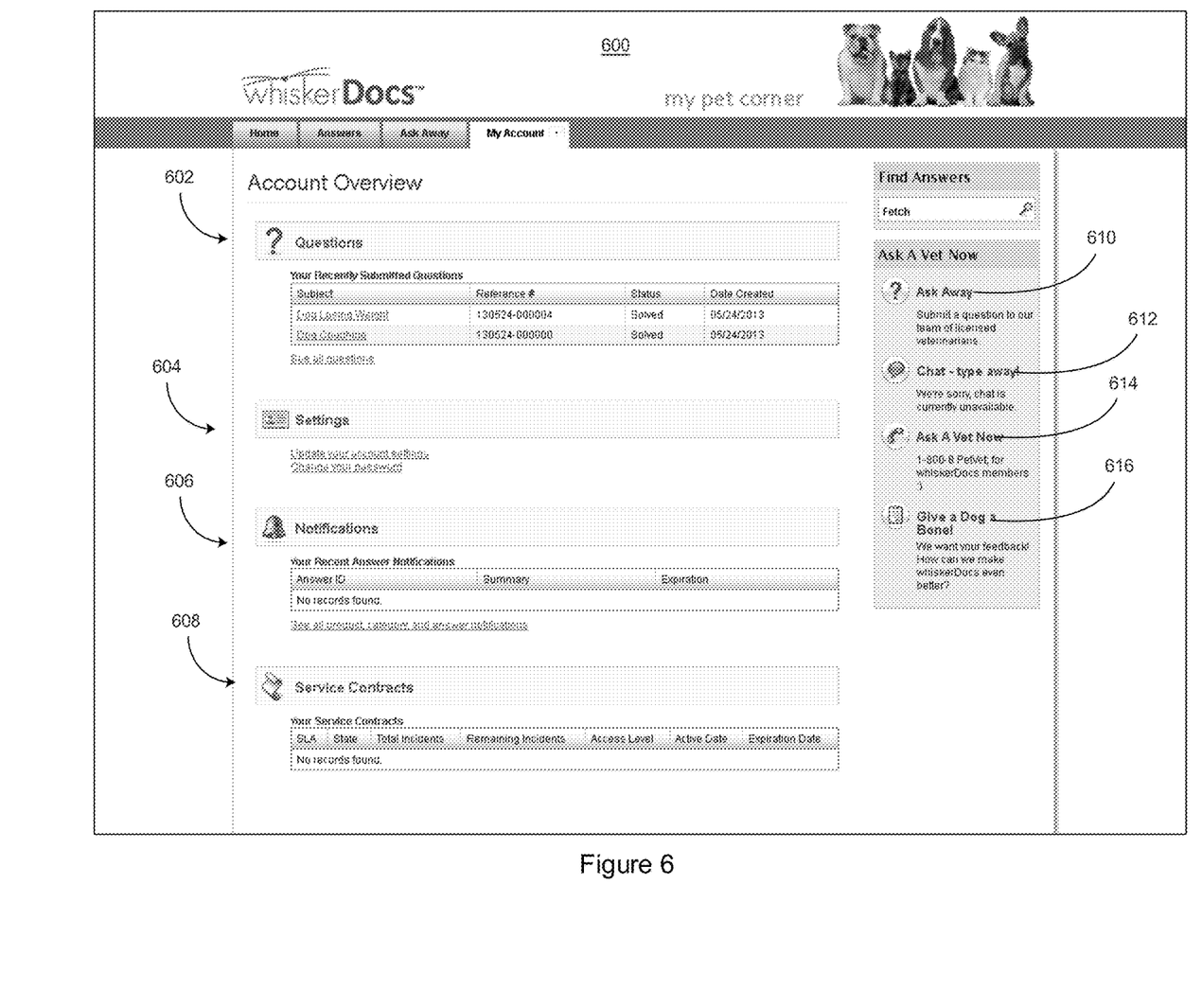
FIG. 6 shows an exemplary screenshot of a user account page on a web portal.

In some embodiments, the system 10 may include an administration application 60. The administration application 60 may be provided by the server 40, for example, as a stand-alone application running on a computer such as a workstation computer, laptop computer, handheld computer, tablet, mobile messaging device, or the like which may all utilize different hardware and/or software packages. Alternatively, or additionally, administration application 60 may connect to the server 40 via the Internet using a standard browser application. A browser based implementation allows system features to be accessible regardless of the underlying platform of the administration application 60. Other methods may be used to implement the administration application 60. As should be apparent to one of ordinary skill in the art from the disclosure herein, other related services may also be provided. An exemplary screenshot of a user interface for an administration application 60 is shown in FIG. 6.

2.0 Exemplary Decision Support Process

Figure 2:
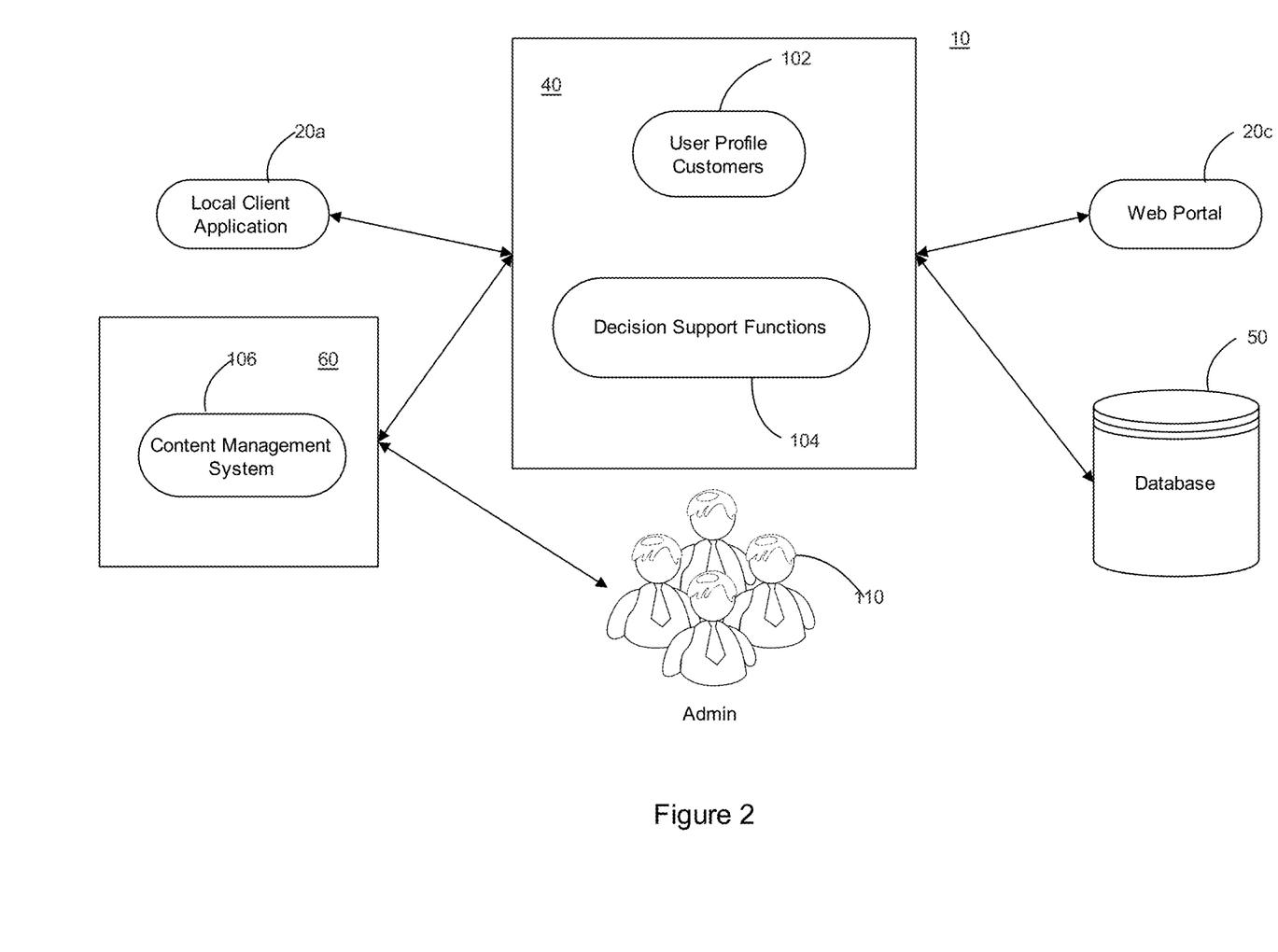
FIG. 2 shows an exemplary functional architecture for an exemplary system for answering a pet health query.

FIG. 2 shows an exemplary functional architecture of one embodiment of decision support system 10. Decision support server 40 may provide a way for local client application 20a-c to access user account functionality 102 and decision support functionality 104 as well as database 50. In addition, content management functionality 106 may be accessible via the administration application 60 as described above.

2.1 Exemplary User Account Functions

In some embodiments, users may access a user account functions 102 to create an account. A user also may access a portal on a local client application on one of the devices listed above. A user may access a customer portal on a client application 20c of a local computing device, for example, by requesting the customer portal from a web server. Several components of the system may apply whether the user is logged in to his or her account or not, although additional components may be available to logged in users. For example, both logged out and logged in users may be able to progress through question sets, as discussed below, but responses entered by a logged in user also may be added to a record generated for the user or pet, which may be formatted and/or transmitted to the user's veterinary provider.

On subsequent "Create a Profile" pages, the system may present further queries and fillable fields to the user regarding additional pet demographic and health information, including but not limited to age, gender, species, breed, and pre-existing conditions, for each pet entered by the user. The system also may include an option to upload other documents related to a health record of a pet, including past records from a veterinarian. Any uploaded files may be stored in a database of the system, such as database 50, and may be accessible to the user upon logging in and accessing the account tab on the customer portal homepage.

The user account or profile may be stored in the database associated with the cloud customer relationship management (CRM) platform, and the user may be returned to the customer portal homepage, thereby completing the registration process. Again, this information may be submitted at a different time, such as during part of the decision support process, although it may be beneficial to provide it at an outset so that it may be available readily across multiple query sessions at different times.

Figure 3:
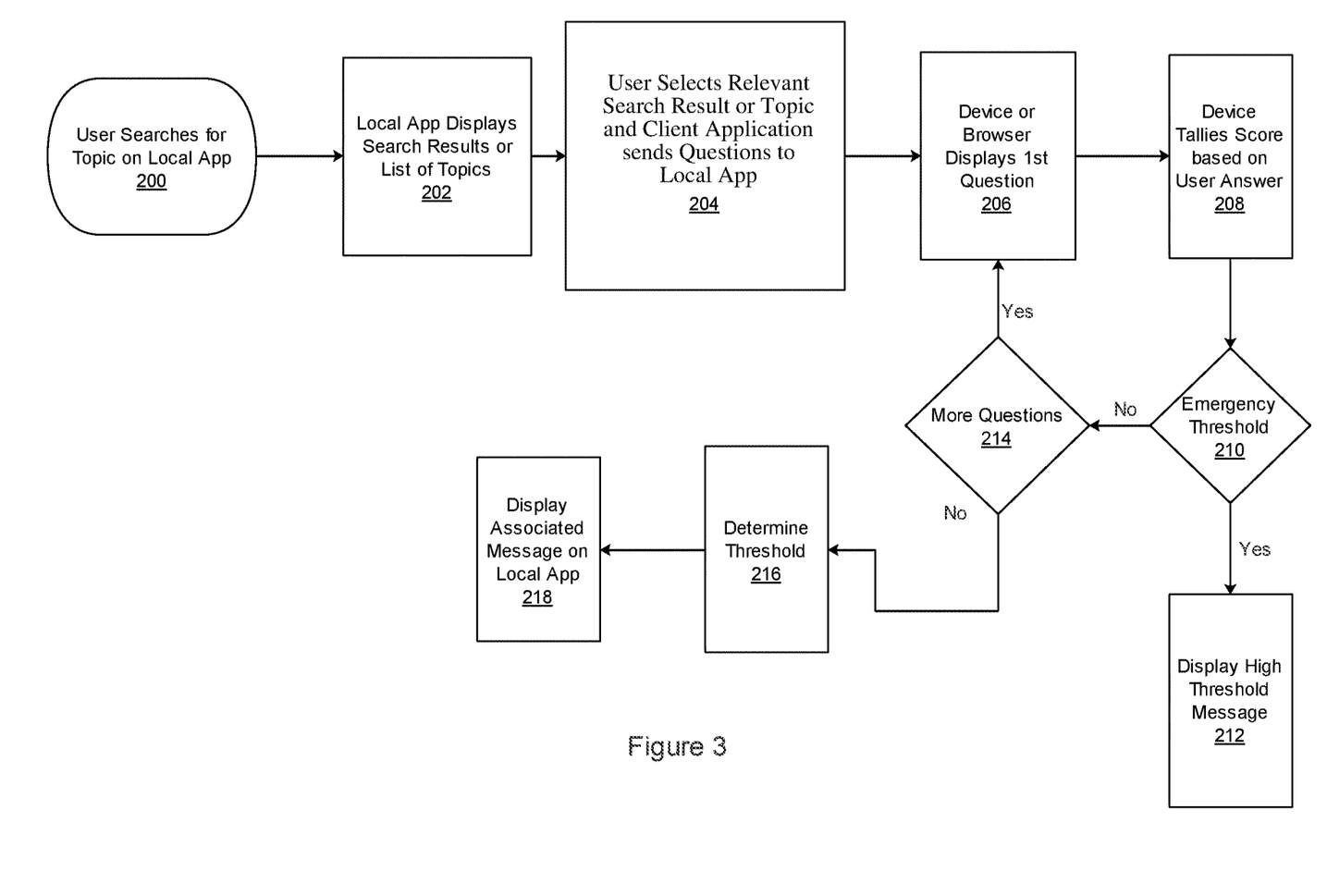
FIG. 3 shows an exemplary flowchart for answering a pet health query.
Figure 4A:
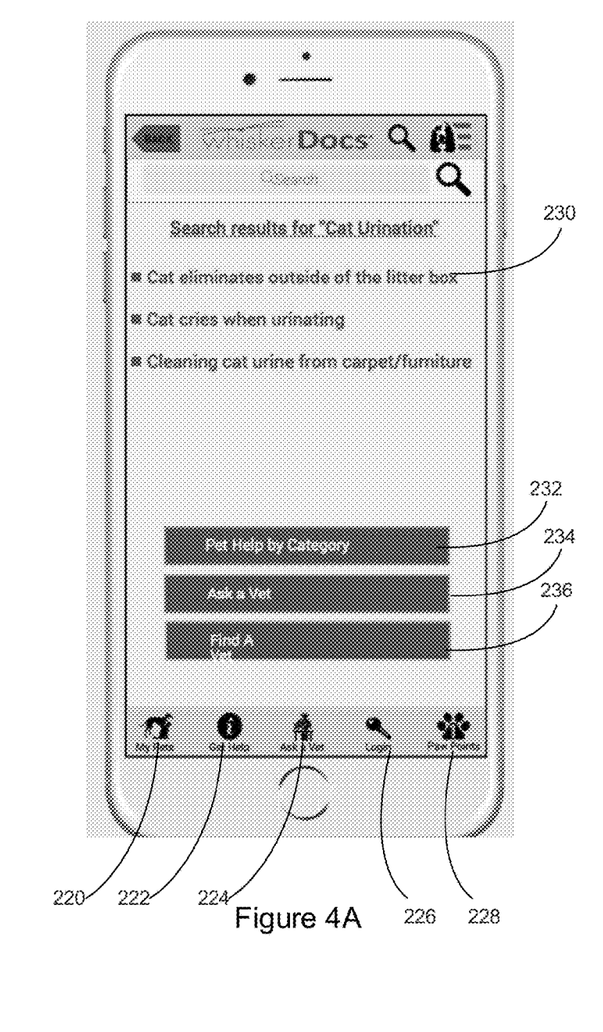
FIGS. 4A-4H show exemplary screenshots of a client application showing the system answering a pet health query.

2.2 Exemplary Decision Support Functions 104 and Exemplary Decision Support Process Users may access decision support features 104, such as question sets and the like, in a variety of ways. FIG. 3 shows a flow chart of an exemplary decision support process. When a user with a pet related query needs advice, the user may begin by searching at step 200 for a pet's symptoms or other health topic on the local client application 20*a*. The decision support server 40 may return search results from a database in step 202 (and shown in the exemplary screenshot shown in FIG. 4A). Local client application 20*a* may display a list of search results 230, along with other icons for alternative actions. Alternatively, or additionally, client application 20*a*-*c* may display a list of question sets for a user to select without first performing a search at step 202. In some embodiments, question sets may be provided in a list that may be organized by topics, sub topics, or the like.

The user may then select a relevant topic at step 204. The decision support server 40 may then send some a question set to local client application 20*a*. The local client application 20*a*-*c* may store the question set and answers and may not need any additional input from the server 40 and/or database 50 where the user answers questions in the question set. In some embodiments, the client application 20*a*-*c* may compare a stored version of the question set for a particular topic with that stored by server 40 and download a copy of the question set only if the server 40 has an updated version of the question set. By downloading an entire question set in this manner, the system 10 is able to utilize a thin client application 20*a*-*c* that may implement the most update to date decision support functionality and question sets without needed to be recompiled and redistributed to users.

Question sets may include several pieces of information, such as header information, scoring threshold information, question information, answer information, decision information, and the like. Question sets also may include various types of questions. Preferably, the questions have predefined answers and scores and may be linked to at least one other question in the set. For example, in some embodiments, a question may have a number of mutually exclusive answers, such as a yes/no question. Yes/no questions may have two answers to a question, yes or no, and provide the same or different score for each answer. Similarly, a multiple choice question may allow a user to select one answer from a list of two or more answers and also may assign a score to each answer choice. Another question type may allow a user to select zero or more answers, such as a list of symptoms.

Figure 4B:
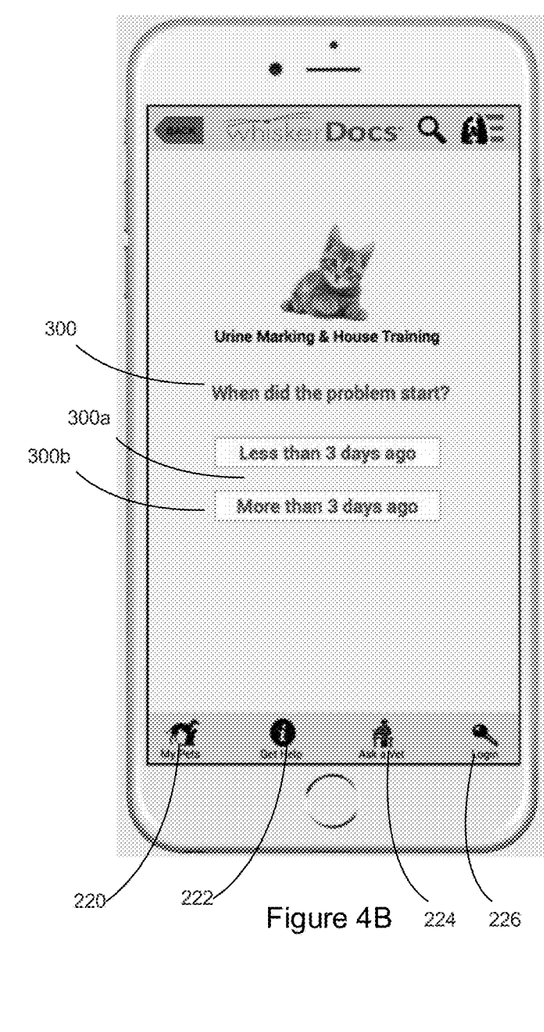
Figure 4C:
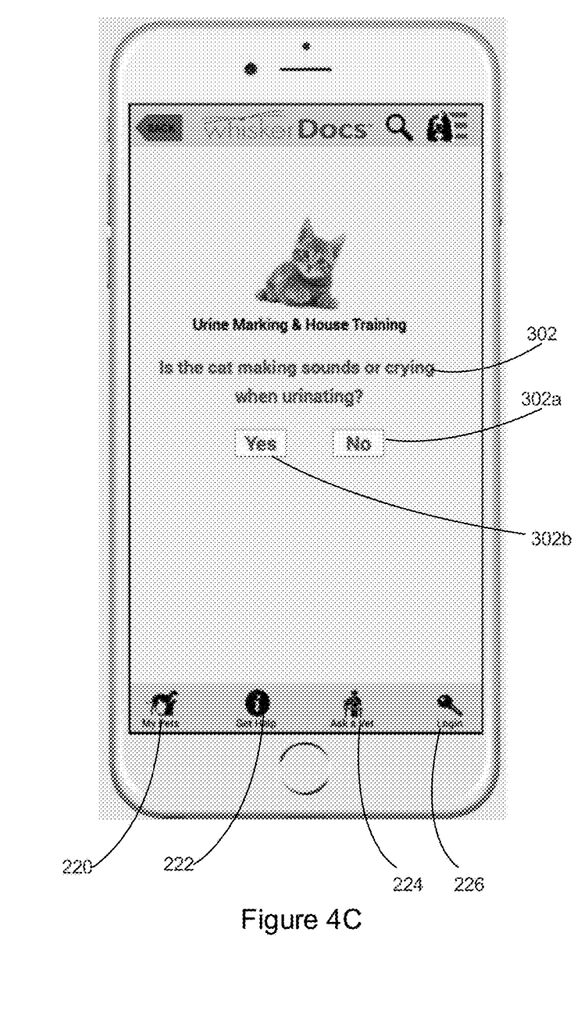
Figure 4D:
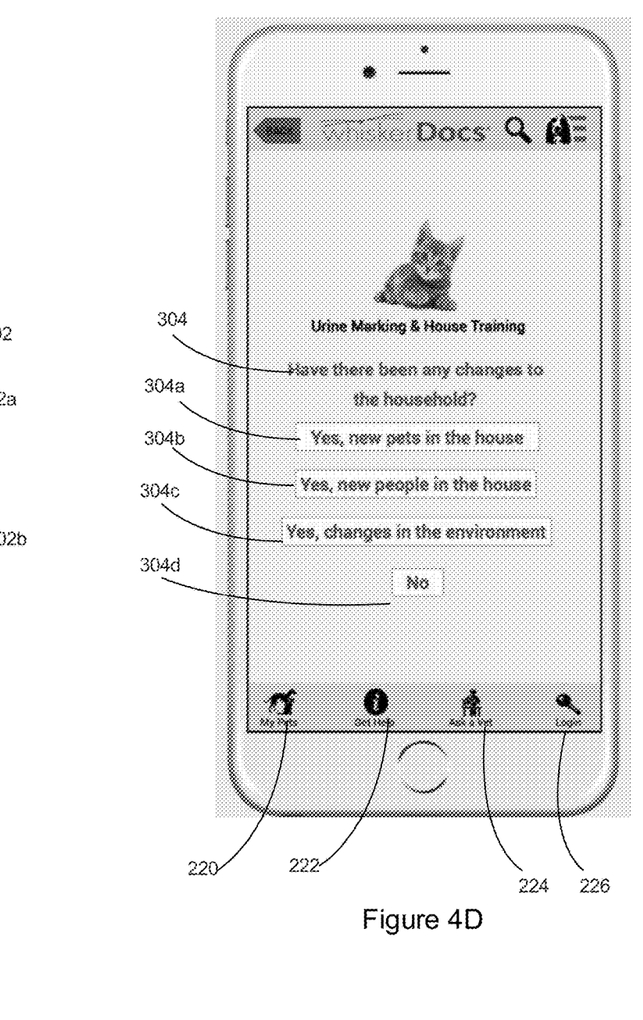
Figure 4E:
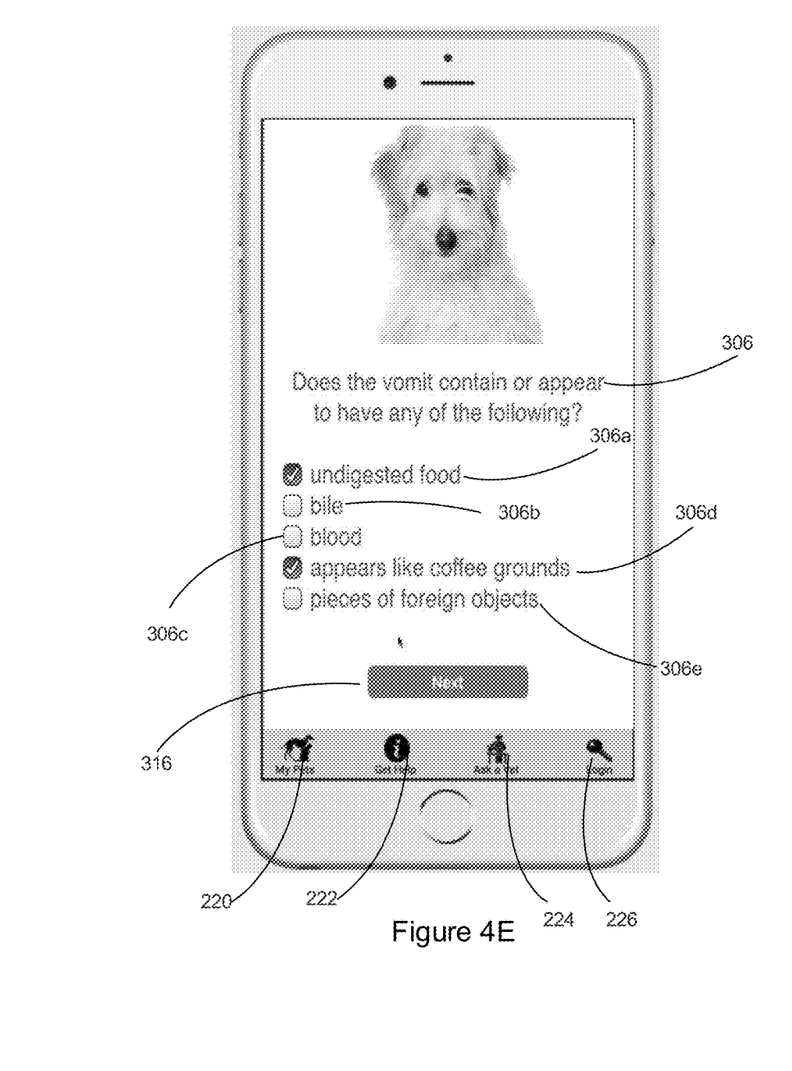

An exemplary yes/no question as shown in FIG. 4C. Local client application 20*a* may display exemplary question 302 and answers 302*a* and 302*b*. An exemplary multiple choice question as shown in FIG. 4D. Local client application 20*a* may display exemplary question 304 and answers 304*a*, 304*b*, 304*c*, and 304*d*. An exemplary zero or more question as shown in FIG. 4E. Local client application 20*a* may display exemplary question 306 and answers 306*a*, 306*b*, 306*c*, 306*d*, and 306*e*.

Referring again to FIG. 3, the client application then may display the first question to the user at step 206, as shown in the exemplary screenshot in FIG. 4B. In some embodiments, these questions also may comprise questions that do not contribute to the score, such as background questions. These background questions may include the pet's age, sex, duration of symptoms, or the like. Exemplary question 300 and answers 300*a* and 300*b* may be used to gather background information.

Each question in a question set may have one or more associated answers. In some embodiments, each answer may be assigned a score. As users select answers, a cumulative score may be tallied and various messages may be displayed based on the score or total score. For example, scores may be multiplied, divided, or otherwise manipulated based on user inputs and for system parameters. System 10 also may allow users to enter a score for a question. In some embodiments, scores may be tallied by the client application 20*a*-*c*. Alternatively or additionally, scores may be tallied by the decision support server 40.

In some embodiments, question sets also may include score values for pet demographic and health information. The pet demographic and health information may include, for example, age, gender, species, breed, heredity and pre-existing conditions, for a pet. Pet demographic and health information may be entered by the user, as noted above, or may be imported from health pet records, such as pet demographic and health information extracted from veterinarian records, other pet health applications, or any other source. For example, an age field may be included in a question set that assigns scores to specific ages or ranges of ages. As another example, a question set also may include a list of pre-existing conditions, such as diabetes, heart murmurs or the like, as well as scores for those conditions. Scores for each demographic and/or health data point may vary from question set to question set to reflect their relevance to a given health condition.

Multiple health and demographic data points may be combined and assigned a single score. For example, a male, 10-year dog with diabetes may be given a predetermined score. Alternatively, or additionally, scores for each data point may be mathematically manipulated if certain combinations of factors are present. For example, a male dog may be given a first score, a 10-year old dog may be given a second score, and a dog with diabetes may be given a third score, and these score may be added or otherwise combined to score a 10-year old male dog with diabetes. Other scoring systems also may be used.

In some embodiments, the system 10 also may incorporate answers to previous question sets. For example, answers to questions (or entire question sets) may be stored for later retrieval, such as to share with a veterinarian or the like. The system 10 may analyze previous responses to incorporate into the pet's health record. The system 10 also may provide scores for a current question set based on these previous answers, either directly from analyzing the responses or indirectly from the updated health record of the pet. In some embodiments, the relevance of previous answers may be time gated so that certain temporary conditions, such as vomiting, expire after a given time.

Referring again to FIG. 3, after the user answers a question, local client application 20*a* will tally the score from the answer or answers at step 208. Local client application 10 may use other methods to calculate a score. For example, a score may be programmed into a preceding question's answer's scores, thus when the local client application 20*a* reaches a final question, the answer scores will reflect the scores from all of the preceding answers without the need for the local client application to perform mathematical functions.

Figure 4F:
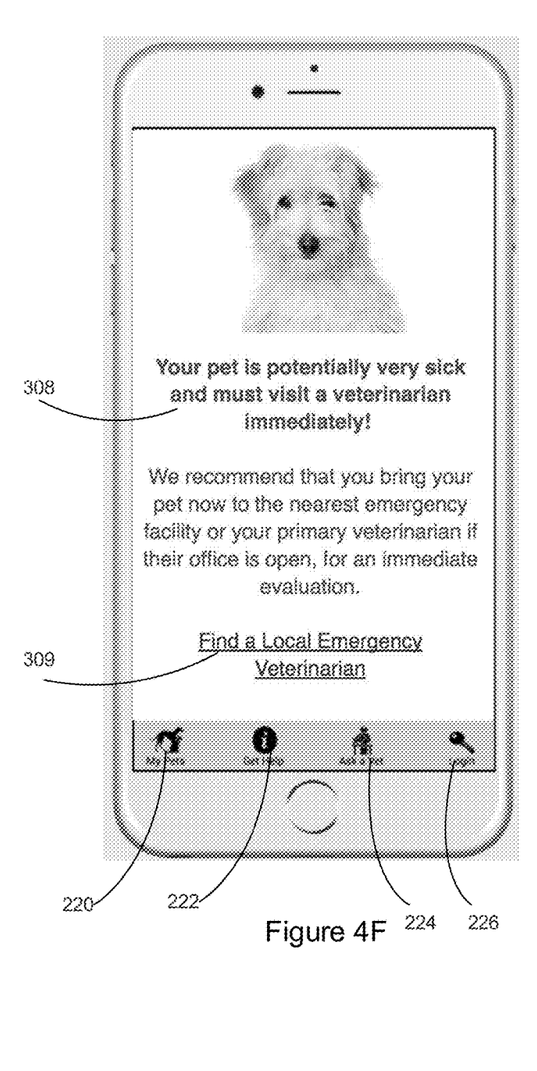

If the score is over a certain emergency threshold 210, local client application 20*a* may display emergency threshold message 212, also shown in the exemplary screenshot in FIG. 4F. This threshold may be about 25. For example, this may tell the user to bring their pet to an emergency vet immediately, such as message 308. In addition to message 212, local client application 20*a* also may display a link to allow a user to search for a local veterinarian or the like.

Returning to FIG. 3, if the score fails to reach the emergency threshold 210, the local client application 20*a* may determine if there are additional questions 214 based on the questions sent previously at step 204. If there is another question, local client application 20*a* may return to step 206. Once local client application 20*a* loops until there are no remaining questions at step 214, the device may display a message based on the total score.

Figure 4G:
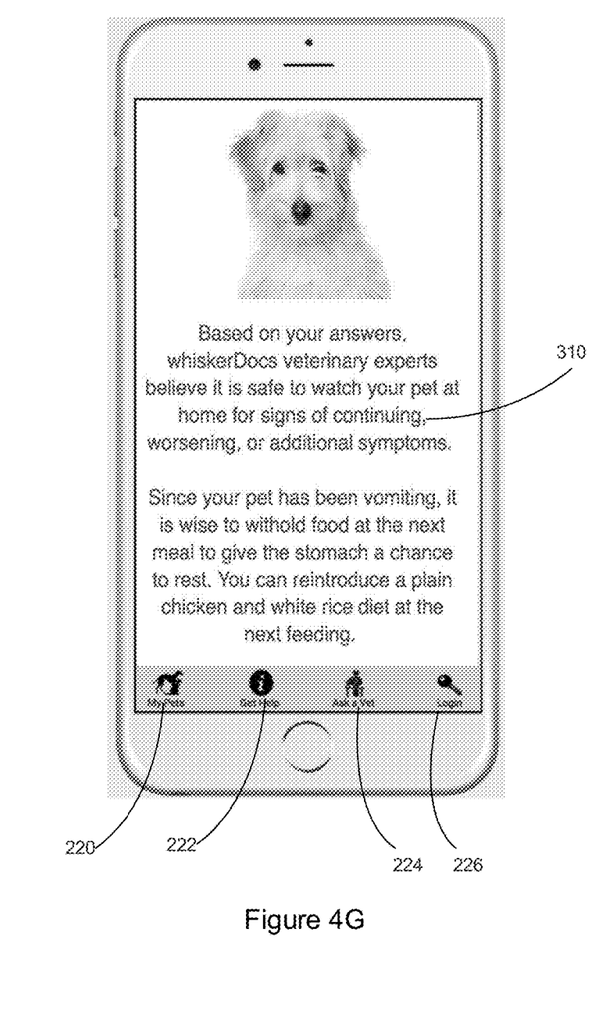
Figure 4H:
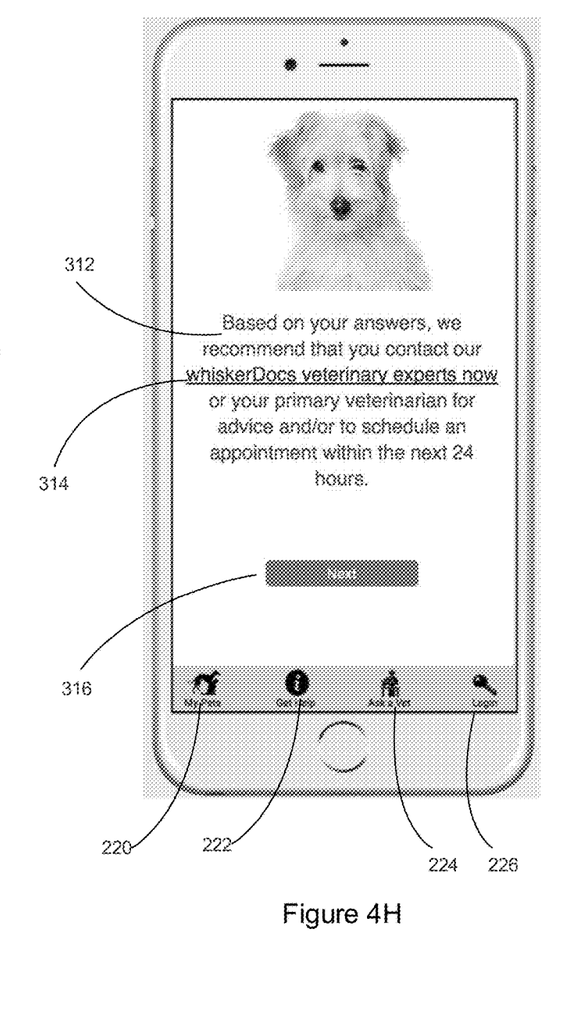

At step 216, the local client application will determine the score and determine which score threshold has been reached. Local client application 20*a* then may display a message associated with the threshold at step 218. As shown in the exemplary screenshot in FIG. 4G, this message may tell the user to monitor their pet closely, as shown in message 310. As shown in the exemplary screenshot in FIG. 4H, this message may tell the user to schedule an appointment soon with the vet, as shown in message 312. In addition to displaying message 312, the local client application 20*a* also may display a link to allow a user to contact a veterinarian or like using a system messaging or system chat feature.

System 10 may include additional or fewer score thresholds and corresponding messages. The preceding scores and thresholds are merely exemplary, and any score may be used to set up different alert levels based on the specific questions asked.

Figure 5:
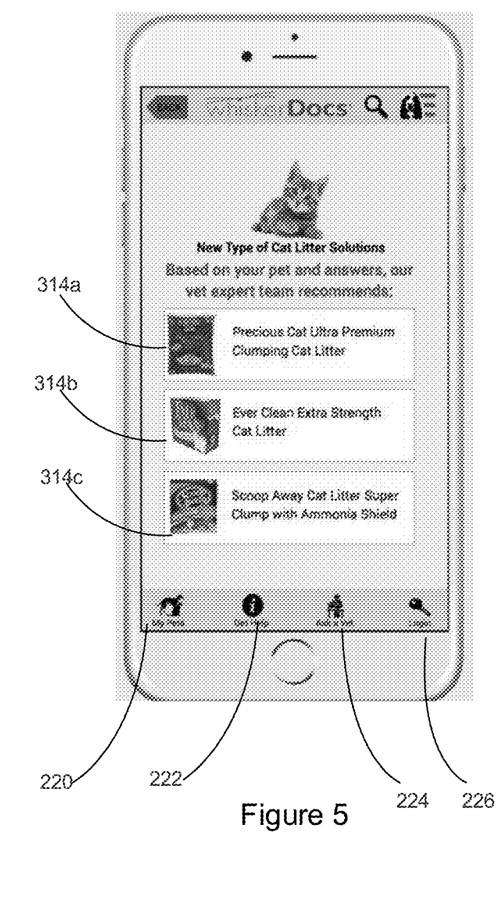
FIG. 5 shows an exemplary screenshot of a client device showing links for related products.

As shown in FIG. 5, local client application 20*a* also may, after obtaining a result from the above steps, display hyperlinks 314*a-c* to a user that are relevant to their pet query. These hyperlinks may include links to other documentation or information about the query and/or links to products relevant to the query. An exemplary screenshot showing these links is shown in FIG. 5.

2.3 Exemplary Content Management Features

Content management system 106 may allow an administrator 110, such as a vet team, or the like, to edit the questions on database 50 through decision support server 40. The questions may be stored on database 50 and accessed through decision support server 40. This allows for easy updates to the questions without altering local client application 20*a*. When a user opens a local client application 20*a* and an internet connection is active, the application checks with decision support server 40 if it has the most up to date copy of relevant questions and downloads the newest questions if it was out of date. If there is no network connection available at the time, the client application 20*a* may use the stored question set.

3.0 Exemplary Data Elements 3.1 Exemplary Question Set Data

As noted above, question sets may include several pieces of information, such as header information, scoring threshold information, question information, answer information, decision information, and the like. More or less information also may be included in a question set. In some embodiments, question sets may be stored in an open source format, such as JavaScript Object Notation (JSON) or the like. Exemplary code which may be used to implement CA 100 and database 50 may be found in Appendix A.

3.1.1 Exemplary Question Set Header Data

Questions set header information may include meta information for a particular question set. The following is an exemplary definition of a question set header:

```
{
  "ca": {
    "ext-desc": "If your dog or cat is not eating, it may be a sign of a larger problem.",
    "id": "ANOREXIA-1",
    "int-desc": "anorexia/not eating clinical algorithm for app",
    "title": "Anorexia & Not Eating",
    "use-by-system": "both"
  },
}
```

In the example above, the "extdesc" field may be text used to describe the pet health topic for the set of questions to answer. The "id" field may be a unique identifier for the question set. The "intdesc" field may be an description used by content managers for the questions set. The "title" field may be a title for the topic associated with the question set. The "usebysystem" fields may provide information about the type of client application 20*a-c* that may access the question set.

3.1.2 Exemplary Question and Answer Information

An exemplary definition of a question may include an identifier for the question, question text, a question type and one or more answers. More or less information also may be included in the definition of a question. Each answer may be defined to include an identifier, answer text, a score associated with selection of the answer, additional information associated with the answer (such as a further explanation about the answer and the like) and a link to the next question to be asked upon selection of the answer. In some embodiments, links to the next question to be asked in the question chain may be included in the definition of the question, rather than the answer.

An exemplary definition for a yes/no question may be as follows:

```
{
  "id": "3",
  "text": "Does you cat tear apart or eat toys, yarn, or other inanimate objects?",
  "answer-type": "yes-no",
  "answers": [
    {
      "id": "1",
      "text": "Yes",
      "score": "20",
      "tip": "Cats that eat yarn or strings can develop a condition that is called a string foreign body requiring surgical intervention",
      "next-question-id": "4"
    },
    {
      "id": "2",
      "text": "No",
      "score": "0",
      "next-question-id": "4"
    }
  ]
},
```

In the above example, the "id" field may identify the question in the numbered sequence of the question set. The "text" field may provide the text of the question to be displayed. The "tip" field may define a pet health related tip that is associated with a particular question or answer. The "answer" field may define possible answers for the particular question. As noted above, each answer may include its own definition. For example, the "id" field may identify the answers in a particular question. The "text" field may include the text of the answer to be displayed. The "answertype" field may define the type of question, such as "yesno," "multiple," or "ZeroOrMore," to represent yes or no questions, multiple choice questions, or zero or more questions respectively. The "nextquestionid" field may be used to move to a new section of code when a user inputs a particular answer. The "nextquestionid" field may use a terminator to signal the end of the list of questions, such as "end." The "score" field may provide the score for the local client application 20a to tally.

An exemplary definition for a zero or more question may be as follows:

```
{
  "id": "6"
  "text": Several factors can influence snoring, select which apply.",
  "answer-type": "zeroormore",
  "answers": [
  {
  "id": "0",
  "nextquestionid": "end"
  },
  {
  "id": "1",
  "nextquestionid": "end",
  "score": "1",
  "text": "Overweight"
  },
  {
  "id": "2",
  "nextquestionid": "end",
  "score": "2",
  "text": "Nasal Problems"
  },
  {
  "id": "3",
  "nextquestionid": "end",
  "score": "3",
  "text": "High Blood Pressure"
  }
  ],
}
```

In the above example, the "id" field may identify the question in the numbered sequence of the question set. The "text" field may provide the text of the question to be displayed. The "tip" field may define a pet health related tip that is associated with a particular question or answer. The "answer" field may define possible answers for the particular question. As noted above, each answer may include its own definition. For example, the "id" field may identify the answers in a particular question. The "text" field may include the text of the answer to be displayed. The "answertype" field may define the type of question, such as "yesno," "multiple," or "ZeroOrMore," to represent yes or no questions, multiple choice questions, or zero or more questions respectively. The "nextquestionid" field may be used to move to a new section of code when a user inputs a particular answer. The "nextquestionid" field may use a terminator to signal the end of the list of questions, such as "end." The "score" field may provide the score for the local client application 20a to tally. A zero or more question may indicate an "id" field equal to zero, which may be used by the system to indicate that a user has not selected any answer for the question. In some embodiments, a score may be associated with a response in which the user does not select any of the answer choices.

3.1.3 Exemplary Scoring Threshold Information

Exemplary code for setting thresholds may be:

```
"scoring": {
  "see-vet-threshold": "10",
  "er-threshold": "25"
},
```

The "see-vet=threshold" field may define the cumulative score required to recommend that the use see a vet, such as within a day, a week, or a month. The "er-threshold" may define the cumulative score required to identify an emergency condition and/or recommend that the user take their pet to the vet immediately. Cumulative scores falling below either threshold may trigger a different response or recommendation from the system, such as at home care, monitoring of the situation, or the like.

3.1.4 Exemplary Course of Action Information

Exemplary code for implementing the displayed result or course of action messages may be:

```
"results": {
  "id": "end",
  "text": "Based on your answers, we recommend:",
  "result": [
    {"id":"watchful_care", "text":"Watchful care of your pet at home. If symptoms worsen, contact your vet immediately."},
    {"id":"see_vet", "text": "Calling your local vet and making an appointment as soon as possible."},
    {"id":"er", "text":"This is an emergency. Take your pet to the closest emergency clinic now."}
  ]
}
```

When a preceding "nextquestionid" is "end" the program will jump to the "results" field and display the contents of the "text" field depending on the threshold reached.

3.1.5 Exemplary Data for Storing Answers for a Question Set

An exemplary data set for storing answers to a question set may be as follows:

```
{
  "ca-completed": {
    "id": "89734897",
    "pet-id": "12839082",
    "ca-id": "ANOREXIA-1",
    "total-score": 12,
    "result": "see_vet",
    "date": "01-31-2016",
    "answ-completed": [
```

```
        {
            "question-id": "1",
            "answer-id": "4"
        },
        {
            "question-id": "2",
            "answer-id": "2"
        },
        {
            "question-id": "3",
            "answer-id": "2
        }
      ]
    }
  }
}
```

The "id" field may define a unique identifier for the completed question set. The "pet-id" field may define identifier for the pet associated with the answers. The "ca-id" field may define the question set that was answered by the user. The "total-score", "result" and "date" fields may define the cumulative score for the given answers, the recommended course of action, and the date on which the recommendation was given, respectively. The "answ-completed" field may define the identifiers of the questions and selected answers for each question in the set answered by the user.

3.2 Exemplary Search Result or Topic List Information

An exemplary definition of search results or a topics list may be as follows:

```
{
"cametas": [
    {
      "code": "NOTEAT01",
      "desc": "If your dog or cat is not eating, it may be a sign of a larger problem.",
      "lastupdated": "20160827",
      "title": "Not Eating",
      "url": "https://appspot.com/_ah/api/wd/v2/ca?code=NOTEAT01"
    },
    {
      "code": "BADBRE01",
      "desc": "Bad breath can be caused by many factors, some have simple solutions, others
      are more serious.",
      "lastupdated": "20160827",
      "title": "Bad Breath",
      "url": "https://appspot.com/_ah/api/wd/v2/ca?code=BADBRE01"
    },
    {
      "code": "CONSTI01",
      "desc": "Constipation for your dog or cat is not only uncomfortable
      but can be a severe
      issue.",
      "lastupdated": "20160827",
      "title": "Constipation",
      "url": "https://appspot.com/_ah/api/wd/v2/ca?code=CONSTI01"
    }
  ]
}
```

The search results and/or topic lists may be stored in lists of API accessible lists. The "cametas" field may signal the list of pet health topics. The "code" field may signal a particular pet health topic. The "desc" field may provide a description of the pet health topic. The "lastupdated" field may provide a date that the particular topic and questions was last updated. The "title" field may provide the title of each pet health topic. The "url" field may provide the uniform resource locator address for each pet health topic question set to a local client application 20a to allow it to download the question set.

3.3 Exemplary Pet Health Record

An exemplary definition of pet heath record may be as follows:

```
{
  "pet": {
      "id": "12839082",
      "name": "Whiskers",
      "type": "Cat",
      "age": "4",
      "birthday": "05-22-2012",
      "gender": "Female",
      "breed": "American Shorthair",
      "spayed": "Yes",
      "weight-kg": "5",
      "med-cond": [
          {
            "id": "DIABETES-2",
            "desc": "Diabetes",
            "onset-date": "08-01-2016",
            "rem-date": "NA",
            "medication": "Basaglar"
          },
          {
            "id": "HYPOTHRY-1",
            "desc": "Hypothyroidism",
            "onset-date": "02-19-2016",
            "rem-date": "NA",
            "medication": "Felimazole"
          }
      ],
      "ca-completed": [
          {
              "id": "ANOREXIA-1",
              "result-set-id": "89734897",
              "result": "see_vet",
              "date": "01-31-2016"
          }
      ]
  }
}
```

The "idt" field may define a unique identifier for the pet. The "name" field may define the pets name. The "type" field may define the type of animal, such as cat, dog or the like. The "age" and "birthday" fields may define the pet's age (which may be calculated by the system) and birthday, respectively. The "gender" and "breed" fields may define the pet's gender and breed, respectively. The "spayed" field may define whether the pet was spayed or neutered. The "weight-kg" field may define the pet's weight in kilograms. Other units also may be used. The "med-cond" field may define zero or more past or current medical conditions of the pet, such as diabetes, hypothyroidism and the like. For each medical condition, an identifier and description of the condition may be stored along with an onset date and a remediation date, if applicable, as well as any medications that may have been prescribed and/or taken to treat the condition.

In some embodiments, records of previously completed question sets also may be stored in a pet's health record. In the above example, an identifier of the question set and the stored answers may be stored in the "id" and "result-set-id" fields, respectively. In addition, the recommended course of action and date of the recommendation also may be stored in the "result" and date fields, respectively.

4.0 Other System Functions

FIGS. 4A-4E and 5 show exemplary screenshots that local client application 20a may present to a user. The following example references local client application 20a, but the process may be similar for local client applications 20b and 20c. The screens for other local client applications 20b and 20c may be similar and/or display similar screen elements. Each screen may include navigation icons on the local client application 20a to aid the user in using the application. These may include a My Pet icon 220, a Get Help icon 222, an Ask a Vet icon 224, a Login icon 226, a Paw Points icon 228, a Care Library icon 238, an Account icon 240 and a Next button 316. Additional or fewer icons may be used to aid user navigation. The My Pet icon 220 may allow a user to access a page containing their pet data, which may have been stored previously or may be added. The Get Help icon 222 may allow a user to access a help page to provide guidance in how to use local client application 20a. The Ask a Vet icon 224 may allow a user to contact a veterinarian, which may be done as a live or non-live chat. The Login icon 226 may allow a user to log into their account or change their login status. The Paw Points icon 228 may allow a user to access their rewards points page. The Care Library icon 228 may allow a user to access a plurality of health articles about their pets. The Account icon 240 may allow a user to access their account screen, where she can manage and change account attributes. The Next button 316 may be used to navigate to a subsequent screen, menu, or question in the question set.

Turning now to FIG. 6, a screenshot of a customer account summary that is accessible by a registered user is shown. As may be seen from this figure, in the system 10, a registered user may be able to access previously-created reports or pet health record entries by logging into the account, selecting the "My Account" tab from the customer portal homepage, and then selecting the report or health record entry by selecting an identifying link pertaining to that report/entry.

The health record may be accessible from any local client application 20c having access to the internet. All of the questions the user asked a veterinarian using the system regarding a pet health issue are shown under Your Recently Submitted Questions heading 602. This may include a Status area which may display the status of the questions, i.e., whether they are solved or unsolved. The Settings heading 604 allows the user to change certain settings, such as account settings or change their password. The Notifications heading 606 displays any answers sent to the user to recently asked questions. The Service Contracts heading 608 may display current and past service contracts associated with a given user.

The "My Account" tab also may include quick access links to quickly reach a veterinarian or the like. The Ask Away link 610 may allow a user to submit a question to a veterinarian. The Chat link 612 may allow a user to chat with a veterinarian. The Ask a Vet Now link may provide a user a phone number to call a veterinarian from a telephone. The Give a Dog a Bone link 616 may allow a user to provide feedback to a system administrator or the like concerning system 10.

While the foregoing written description enables one of ordinary skill to make and use the same, those of ordinary skill also will understand and appreciate the existence of variations, combinations, and equivalents of the specific exemplary embodiments and methods disclosed herein within the scope and spirit of the claims.

We claim:

1. A system for providing non-human animal health care decision support, comprising:

a first software module for use on one of a personal computing device or a mobile device, the software module including instructions stored on a non-transitory computer readable medium that:

collect from a user information about a non-human animal including type of non-human animal;

present a non-human animal health topic to a user;

receive a selection of the non-human animal health topic from the user;

request, from a server computer, a question set related to the non-human animal health topic, the question set including one or more questions, each question having one or more associated answers;

receive, from the server computer, the question set;

display one or more questions from the question set;

receive selections of answers associated with the displayed questions;

determine a course of action based on the selected answers, wherein the course of action is a recommendation comprising at least one of contacting a veterinarian, making an appointment with a veterinarian, watching for change in symptoms in the non-human animal, or transporting the non-human animal to a clinic, store the recommended course of action and date of the recommendation; and display the determined course of action; and a second software module for use on a server computer, the second software module including instructions stored on a non-transitory computer readable medium that:

receive the request for the question set related to the non-human animal health topic; and transmit a question set related to the non-human animal health topic, the question set including one or more questions, each question having one or more associated answers.

2. The system of claim 1, where each answer has an associated score and where the instructions that determine the course of action further comprise instructions that determine the course of action by adding the scores associated with each selected answer.

3. The system of claim 2, where the question set includes data elements that correspond to the one or more predetermined thresholds, including a threshold associated with an emergency condition and a threshold associated with at home monitoring of an animal.

4. The system of claim 1, where each answer in the question set is linked to either another question in the set or a terminator.

5. The system of claim 1, where the collecting step also includes at least one of a gender of the non-human animal and specifying whether the non-human animal is spayed or neutered.

6. The system of claim 1, where the second software module further includes instructions that receive a search request for topics associated with one or more keywords, determine one or more topics related to the one or more keywords and provide hypertext links to questions sets associated with the one or more topics.

* * * * *